US010282489B2

(12) United States Patent
Fisker

(10) Patent No.: US 10,282,489 B2
(45) Date of Patent: May 7, 2019

(54) DESIGNING A DENTAL RESTORATION

(71) Applicant: 3SHAPE A/S, Copenhagen K (DK)

(72) Inventor: Rune Fisker, Copenhagen K (DK)

(73) Assignee: 3Shape A/S, Copenhagen K (DK)

( * ) Notice: Subject to any disclaimer, the term of this patent is extended or adjusted under 35 U.S.C. 154(b) by 0 days.

(21) Appl. No.: 15/907,867

(22) Filed: Feb. 28, 2018

(65) Prior Publication Data
US 2018/0189420 A1    Jul. 5, 2018

Related U.S. Application Data

(63) Continuation of application No. 14/435,826, filed as application No. PCT/EP2013/072202 on Oct. 23, 2013, now Pat. No. 9,934,333.

(60) Provisional application No. 61/717,437, filed on Oct. 23, 2012.

(51) Int. Cl.
| | | |
|---|---|---|
| *A61C 13/00* | (2006.01) | |
| *G06F 17/50* | (2006.01) | |
| *G05B 19/4097* | (2006.01) | |
| *G16H 20/40* | (2018.01) | |

(52) U.S. Cl.
CPC .......... *G06F 17/50* (2013.01); *A61C 13/0004* (2013.01); *G05B 19/4097* (2013.01); *G16H 20/40* (2018.01)

(58) Field of Classification Search
None
See application file for complete search history.

(56) References Cited

U.S. PATENT DOCUMENTS

| | | | |
|---|---|---|---|
| 9,642,685 B2 | 5/2017 | Brodkin | |
| 2007/0154868 A1* | 7/2007 | Scharlack | G05B 19/4097 433/215 |

(Continued)

FOREIGN PATENT DOCUMENTS

WO    WO 2011/159520 A2    12/2011

OTHER PUBLICATIONS

International Search Report (PCT/ISA/210) dated Feb. 24, 2014, by the European Patent Office as the International Searching Authority for International Application No. PCT/EP2013/072202.

(Continued)

*Primary Examiner* — Ryan M Gray
(74) *Attorney, Agent, or Firm* — Buchanan Ingersoll & Rooney PC

(57) ABSTRACT

A method for designing a virtual abutment for manufacturing an abutment part of a dental restoration for a patient, the dental restoration further including a crown configured for being seated at the abutment, wherein the method includes loading a virtual anatomy surface into an electronic data processing device, the virtual anatomy surface expressing a target shape of the crown portion of the dental restoration; loading an obtained virtual abutment including a virtual abutment finish line into the electronic data processing device; and modifying the obtained virtual abutment by executing one or more computer implemented algorithms using the electronic data processing device, where the algorithms are configured to adapt the shape of the obtained virtual abutment such that the virtual abutment finish line of the modified virtual abutment is aligned with the virtual anatomy surface.

11 Claims, 10 Drawing Sheets

(56) References Cited

U.S. PATENT DOCUMENTS

2008/0057478 A1\* 3/2008 Choi .................. A61C 13/0004
 433/215
2009/0111071 A1 4/2009 Yau et al.
2012/0065756 A1 3/2012 Rubbert
2013/0056892 A1\* 3/2013 Johnson ............. A61C 13/0013
 264/19

OTHER PUBLICATIONS

International Preliminary Report on Patentability (PCT/IPEA/409) dated Aug. 22, 2014, by the European Patent Office as the International Searching Authority for International Application No. PCT/EP2013/072202.

\* cited by examiner

DESIGNING A DENTAL RESTORATION

RELATED APPLICATIONS

The present application is a continuation of U.S. Ser. No. 14/435,826, which is a national stage application of PCT/EP2013/072202, filed on Oct. 23, 2013, and which claims the benefit of U.S. Ser. No. 61/717,437, filed on Oct. 23, 2012, and which claims the priority of Danish Patent Application Number PA 2012 70649, filed on Oct. 24, 2012. The subject matter of U.S. Ser. No. 14/435,826; PCT/EP2013/072202; U.S. Ser. No. 61/717,437; and Danish Patent Application Number PA 2012 70649 are incorporated herein by reference.

FIELD OF THE INVENTION

This invention generally relates to a method, a system, and a virtual environment for designing a virtual dental restoration for manufacturing a dental restoration for a patient, said dental restoration comprising an anatomy portion and a sub-gingival portion. More particularly, the invention relates to a method, a system, and a virtual environment where a sub-gingival surface of the designed virtual dental restoration is shaped such that it contacts a virtual anatomy surface of the virtual dental restoration.

BACKGROUND OF THE INVENTION

In some cases where a patient is in need of dental restoration, such as a crown restoration, the tooth or teeth which are to be replaced by the dental restoration are so damaged or weak that an implant needs to be arranged in the patient's bone structure to support the dental restoration. The dental restoration can then be secured at the implant using e.g. a retention screw configured for engaging the bore of the implant and holding the dental restoration firmly in place at the implant.

The dental restoration can be considered to comprise an anatomy portion and a sub-gingival portion, where the anatomy portion is arranged supra-gingival and hence is the visible part of the dental restoration and the sub-gingival portion is the part surrounded by the patient's gingiva when the dental restoration is seated in the patient's mouth.

Different types of dental restorations exist which are adapted for being secured in a dental implant, such as screw retained crowns and an abutment based dental restorations comprising an implant engaging abutment and a crown designed to be seated at the abutment.

For a screw retained crown the anatomy portion and the sub-gingival portion are integrated parts of the dental restoration, such that these portions form a coherent structure.

For abutment based dental restorations, the abutment forms the sub-gingival portion and the crown forms the anatomy portion of the dental restoration. The abutment can be a standard predefined abutment but in many cases the dentist prefers to produce a customized abutment which takes into account the specific situation in the patient's mouth. In the case of a customized abutment a virtual abutment can be designed using dental CAD software, while in the case of a standard abutment the virtual abutment can be provided by the abutment provider. Based on the virtual abutment, the physical abutment can be manufactured using CAM techniques such as milling or 3D printing. In the same manner, a virtual crown part can also be designed based on a digital 3D representation of the patient's set of teeth using CAD software. The crown portion of the dental restoration can then be manufactured based on the virtual crown using CAM techniques.

Often the virtual abutment and the virtual crown are designed separately. Initially a gap between the outer surface of the virtual crown and the outer surface of the virtual abutment may thus occur at the margin line of the virtual crown. This gap has to be closed in order to avoid a grove at the outer surface of the manufactured dental restoration. Such a grove will deteriorate the aesthetic appearance of the manufactured dental restoration and further provide a trap for bacteria and the like.

In prior art methods for designing a dental restoration comprising a crown and an abutment where a gap is occurring between an initial shape of the obtained virtual crown and abutment, the virtual crown is reshaped to contact the virtual abutment. These methods have the disadvantage that the virtual crown is deformed thereby making the appearance of the manufactured crown less attractive and potentially causing discomfort to the patient.

SUMMARY

It remains a problem to provide a method for designing a virtual dental restoration in which the shape and aesthetics of the anatomy portion of the dental restoration is determined by an obtained virtual anatomy portion while a virtual sub-gingival surface of the virtual dental restoration is adapted to contact the virtual anatomy surface such that the appearance of the visible part of the dental restoration manufactured from the virtual dental restoration is determined by characteristics of the obtained virtual anatomy portion.

It remains a problem to provide a method in which the shape and aesthetics of an obtained virtual crown is maintained when connecting the virtual crown with a virtual abutment to form a virtual dental restoration, such that the shape and aesthetic appearance of a crown manufactured from the virtual crown is determined by the obtained virtual crown.

Disclosed is hence a method for designing a virtual dental restoration for manufacturing a dental restoration for a patient, said dental restoration comprising an anatomy portion and a sub-gingival portion, wherein the method comprises:
 obtaining a virtual anatomy surface expressing a target shape of the anatomy portion of the dental restoration; and
 creating a virtual sub-gingival surface for the sub-gingival portion of the dental restoration;
where the created virtual sub-gingival surface is shaped such that it contacts the virtual anatomy surface.

Disclosed is hence a method for designing a virtual dental restoration for manufacturing a dental restoration for a patient, said dental restoration comprising an anatomy portion and a sub-gingival portion, wherein the method comprises:
 loading a virtual anatomy surface into an electronic data processing device, said virtual anatomy surface expressing a target shape of the anatomy portion of the dental restoration; and
 executing one or more computer implemented algorithms using said electronic data processing device, where the algorithms are configured for creating a virtual sub-gingival surface for the sub-gingival portion of the dental restoration;

where the executed computer implemented algorithms are configured to provide that the created virtual sub-gingival surface is shaped such that it contacts the virtual anatomy surface.

In the context of the present invention, the phrase "the created virtual sub-gingival surface is shaped such that it contacts the virtual anatomy surface" refers to the situation where it is the shape of the created virtual sub-gingival surface and not a chance in the shape of the obtained virtual anatomy surface which provides that the virtual sub-gingival surface and the virtual anatomy surface are in contact. The shape of the portion of the virtual anatomy surface which is used for designing the virtual dental restoration is substantially maintained while creating the virtual sub-gingival surface either directly or via an initial virtual sub-gingival surface.

This has the advantage that the target shape the anatomy portion expressed by the obtained virtual anatomy surface is maintained thus avoiding that the planned aesthetic appearance of the dental restoration is distorted.

In some embodiments, the sub-gingival portion of the dental restoration is configured for engaging an implant arranged in the patient's jaw bone.

In the context of the present invention, the phrase "sub-gingival" is used in relation to items, parts, portions or features which are arranged apical to the gingival margin, i.e. items, parts, portions or features which to a large extent are covered by the gingiva and hence are not visible when the dental restoration is seated in the patient's mouth.

In the context of the present invention, the phrase "supra-gingival" is used in relation to items, parts, portions or features which are arranged coronal to the gingival margin, such as the visible parts of a dental restoration when this is seated at the patient's set of teeth.

The margin line of the dental restoration may be arranged such that it is not aligned with the gingival margin. It may for example be advantageous for a dental restoration, such as a dental restoration comprising an abutment and a crown, that the margin line is located below the gingival margin such that the margin line cannot be seen when the dental restoration is secured in the implant. In such cases, a part of the crown surface which extends to a margin line located below the gingival margin can still be considered to be part of the anatomy surface of the dental restoration. In the same manner, the free surface of an abutment, i.e. the part of the abutment outer surface which is not in contact with the inner surface of the crown, is still considered to be a sub-gingival surface even when a minor fraction of it extends above the gingival margin.

When the dental restoration is manufactured from the designed virtual dental restoration, the virtual anatomy surface and the virtual sub-gingival surface together determines the shape of the outer surface of at least part of the dental restoration. In e.g. a screw retained crown comprising the screw itself, the surface of the screw may form the remaining surface of the dental restoration.

The anatomy portion of a dental restoration manufactured from the designed virtual dental restoration is shaped according to at least a part of the virtual anatomy surface while its gingiva-facing surface is shaped according to at least part of the created virtual sub-gingival surface. The sub-gingival surface of the dental restoration is often referred to as the emergence profile of the dental restoration.

The dental restoration may comprise further layers such as a coping layer to be arranged between the abutment and the crown of the dental restoration.

In the context of the present invention, the phrase "the created virtual sub-gingival surface is shaped such that it contacts the virtual anatomy surface" is used in relation to the situation where the two virtual surfaces are brought into close proximity, such as within a distance which is smaller than the precision of the CAM tools used for the later manufacture of the dental restoration. The phrase hence also covers cases where the two virtual surfaces are bought into a relative arrangement where the distance between the corresponding physical units in the manufactured dental restoration is below about 200 micrometers, such as below about 100 micrometers, such as below about 50 micrometers, such as below about 20 micrometers, such as below about 10 micrometers, such as below about 5 micrometers.

In some embodiments, the contact between the virtual anatomy surface and the virtual sub-gingival surface defines a virtual margin line of the virtual dental restoration. The margin line of the manufactured dental restoration may then be determined from virtual margin line.

In some embodiments, the method comprises combining the virtual sub-gingival surface and the part of the virtual anatomy surface coronal to the virtual margin line to form a virtual outer surface of the virtual dental restoration.

The formed virtual outer surface then defines the outer surface of the dental restoration manufactured from the designed virtual dental restoration. Below the margin line the virtual outer surface then takes the form of the virtual sub-gingival surface, and above the margin line its form is determined by the obtained virtual anatomy surface. The virtual sub-gingival surface thus describes the outer shape of the dental restoration where it faces or is in contact with the surrounding gingiva and the virtual anatomy surface describes the outer surface from the incisal edge/occlusal surface of the dental restoration towards the gingiva.

In some embodiments, the method comprises defining an initial virtual sub-gingival surface comprising an initial coronal boundary.

Opposite to the initial coronal boundary the initial virtual sub-gingival surface is preferably bounded by an initial implant facing boundary located e.g. at the implant, such that the initial virtual sub-gingival surface expresses an initial virtual emergence profile for the dental restoration.

In some embodiments, creating the virtual sub-gingival surface comprises:
defining an implant facing boundary for the virtual sub-gingival surface;
projecting the initial coronal boundary of the initial virtual sub-gingival surface onto the virtual anatomy surface to define a coronal boundary of the virtual sub-gingival surface; and
forming the virtual sub-gingival surface such that it extends between the coronal boundary and the implant facing boundary.

In some embodiments, the implant facing boundary for the virtual sub-gingival surface is defined by copying the initial implant facing boundary.

This may be advantageous when the initial implant facing boundary is shaped according to a preferred shape of the virtual sub-gingival surface at the implant, since the implant facing boundary for the virtual sub-gingival surface then automatically also is shaped according to preferred shape.

In some embodiments, the projecting of the initial coronal boundary onto the virtual anatomy surface is substantially parallel to the occlusal plane of the patient.

In some embodiments, the coronal boundary of the virtual sub-gingival surface defines the virtual margin line of the virtual dental restoration.

In some embodiments, the anatomy portion and the sub-gingival portion are integrated parts of a single-piece dental restoration. This may be the case when the dental restoration is a screw-retained restoration, such as a screw retained crown, configured for engaging an implant arranged in the patient's jaw bone. For such dental restorations, the virtual outer surface of the designed virtual dental restoration is preferably a coherent surface.

In some embodiments, an abutment part and a crown part of the dental restoration are separate units and can e.g. be manufactured in different materials. This is e.g. the case when the dental restoration is a two-piece restoration where a crown portion and an abutment portion needs to be connected in order to form the dental restoration. The crown portion can e.g. be cemented to the abutment portion when this has been secured in the implant using a retention screw.

In some embodiments, the dental restoration comprises an abutment portion and a crown portion, where the abutment portion may be an anatomical abutment expressing an anatomical correct shape.

In some embodiments, the sub-gingival portion of the dental restoration comprises an abutment configured for engaging the implant and the anatomy portion comprises a crown configured for being seated at the abutment.

Together the abutment and the crown at least partly form the dental restoration. Other parts, such as a retention screw, may be used for firmly securing the abutment and hence the dental restoration at the implant.

In some embodiments, the method comprises forming part of a virtual abutment surface from the virtual sub-gingival surface and a virtual crown surface from a part of the virtual anatomy surface, such as from the part of the virtual anatomy surface coronal to the margin line. The formed part of the virtual abutment surface then defines at least part of the gingiva-facing part of the dental restoration.

In some embodiments, the method comprises providing a virtual abutment comprising a virtual abutment finish line and creating the virtual sub-gingival surface comprises modifying the virtual abutment such that the virtual abutment finish line of the modified virtual abutment is aligned with the virtual anatomy surface. In that case, the virtual abutment finish line can be used to define the virtual margin line of the virtual dental restoration.

Once the operator is satisfied with the shape of the virtual abutment, the abutment facing surface of the virtual anatomy portion of the dental restoration can be determined by a Boolean subtraction.

In some embodiments, forming the virtual sub-gingival surface comprises executing one or more computer implemented algorithms configured for generating a virtual surface which extends between the implant facing boundary and the coronal boundary, such that the formed virtual sub-gingival surface extends between the coronal boundary and the implant facing boundary.

In some embodiments, creating the virtual sub-gingival surface is performed at least partly by a computer implemented algorithm executed by an electronic data processing device.

One advantage of using a computer implemented algorithm for creating the virtual sub-gingival surface is that such a computer algorithm can perform this task significantly faster than an operator, and in many cases also provide a better result in which the virtual sub-gingival surface is smoother both at its boundaries and in between these.

In some embodiments, the virtual sub-gingival surface is configured to provide a smooth transition to the virtual anatomy surface at the virtual margin line.

This provides that a smooth transition between the anatomy portion and the sub-gingival portion of the manufactured dental restoration is provided.

A smooth transition can be achieved by determining the first derivative of the virtual anatomical surface at the virtual margin line and creating the virtual sub-gingival surface such that its first derivative at the virtual margin line is aligned with the first derivative of the virtual anatomical surface.

When the dental restoration comprises an abutment portion and a crown portion, the smooth transition between the virtual sub-gingival surface and the virtual anatomy surface at the virtual margin line provides a smooth transition between outer surfaces of the crown portion and the abutment portion.

In some embodiments, creating the virtual sub-gingival surface comprises applying a loofting process to form a virtual surface which closes a gap between the initial virtual sub-gingival surface and the virtual anatomy surface.

The loofting process may be configured to provide the gap closing surface as part of the initial virtual sub-gingival surface whereby the virtual sub-gingival surface is formed.

Closing such a gap has the advantage that the outer surface of the dental restoration manufactured based on these virtual surfaces has no groves in which bacteria can be trapped.

Disclosed is a virtual environment for designing a dental restoration comprising a virtual work space adapted for obtaining a virtual anatomy surface expressing a target shape of the anatomy portion of the dental restoration, wherein the virtual environment comprises a virtual tool for creating a virtual sub-gingival surface for the sub-gingival portion of the dental restoration when activated, where the created final virtual sub-gingival surface is shaped such that it contacts the virtual anatomy surface at a margin line of the dental restoration.

In some embodiments, the virtual work space is adapted for defining an initial virtual sub-gingival surface which comprises an initial coronal boundary In some embodiments, the virtual environment is as adapted for defining an implant facing boundary for the virtual sub-gingival surface and wherein said virtual tool when activated provides that computer implemented algorithms are executed, where the computer implemented algorithms are adapted for:

projecting the initial coronal boundary of the initial virtual sub-gingival surface onto the virtual anatomy surface such that a coronal boundary of the virtual sub-gingival surface is defined; and forming the virtual sub-gingival surface such that it extends between the coronal boundary and the implant facing boundary;

where the created virtual sub-gingival surface is shaped such that it contacts the virtual anatomy surface.

In some embodiments, the virtual modification tool is provided as a virtual button, i.e. a virtual button visualized in the virtual environment.

In some embodiments, obtaining the virtual anatomy surface comprises selecting an anatomy surface template from an anatomy surface library.

In some embodiments, obtaining the virtual crown and/or the virtual abutment comprises selecting a crown template or an abutment template, respectively, from a library.

The obtained virtual anatomy surface and/or virtual crown may be designed based e.g. on a digital 3D representation of the patient's set of teeth such that the shape and relative arrangement of the neighboring teeth can be taken into account when designing the virtual anatomy surface and/or virtual crown.

In some embodiments, the modifying of the virtual abutment is performed by virtually snapping the abutment to the crown. The snapping of the abutment to the crown is configured to provide that sections of the outer surfaces of the virtual abutment and the virtual crown are aligned or connected, such that the virtual abutment and virtual crown together defines a smooth outer surface of the dental restoration.

In some embodiments, the virtual abutment is modified in one step, such as when a virtual button in a virtual environment is activated using e.g. a computer mouse.

In some embodiments, modifying the virtual abutment is performed at least partly by a computer implemented algorithm executed on an electronic data processing device.

One advantage of using a computer implemented algorithm for the modifying is that such a computer algorithm can perform this task significantly faster than an operator, and in many cases also provide a better result where the outer surfaces of the virtual crown and virtual abutment provide that the outer surface of the manufactured dental restoration has the most natural appearance.

In some embodiments, the abutment comprises a finish line and the crown comprises a margin line, and modifying the abutment provides that the finish line is aligned with the margin line.

In a dental restoration where the outer surface is defined by the outer surfaces of manufactured crown and abutment portions, the crown margin line and the abutment finish line must preferably be aligned and in contact such that the outer surface of the dental restoration is smooth.

The different lines used in the method, such as the coronal boundary, the implant facing boundary, the finish line of the virtual abutment and the margin line of the virtual crown may be represented by respective 3D splines. The form of these 3D splines and their position can be defined by control points. By moving these control points using e.g. a pointing tool computer an operator can adjust the shape of these 3D splines.

In some embodiments, modifying the virtual abutment is configured to provide that the transition between the abutment and the crown in the manufactured dental restoration is smooth.

The smooth transition can be provided by using a computer implemented algorithm which calculates the tangent of the virtual crown outer surface at the crown margin line and matches this with the tangent of the virtual abutment outer surface at its finish line.

In some embodiments, the method comprises obtaining a digital 3D representation of the patient's set of teeth, said digital 3D representation comprising data relating to a surface of the patient's gingiva, such as data relating to the surface of the gingiva in the vicinity of the implant, i.e. the gingival in an implant region where the dental restoration is to be inserted. The digital 3D representation may in addition to the data relating to the implant region also comprise data relating to the neighbor region surrounding the implant region.

In some embodiments, the initial virtual sub-gingival surface is defined from said data of the digital 3D representation.

This has the advantage that the initial virtual sub-gingival surface can be formed quickly using e.g. a virtual environment configured for implementing the method.

In some embodiments, the initial virtual sub-gingival surface is configured to follow the part of said digital 3D representation relating to the surface of the gingiva in the vicinity of the implant.

This has the advantage that if only minor changes are made when the virtual sub-gingival surface is created based on the initial virtual sub-gingival surface, the sub-gingival surface of the manufactured dental restoration will substantially follow the patient's gingiva.

In some embodiments, the method comprises deriving an emergence profile of the virtual abutment at the implant region from said digital 3D representation. The emergence profile describes the shape of the sub-gingival part of the dental restoration which contacts the gingiva in the implant region when the dental restoration is secured in the implant.

Deriving the emergence profile of the virtual abutment from said digital 3D representation allows the operator to design the virtual abutment taking into account the shape of the gingiva in the implant region. The operator can e.g. decide that the manufactured dental restoration shall apply a gentle pressure to the gingiva when secured in the patient's mouth. This can be achieved by designing the virtual abutment outer surface such that the emergence profile is slightly overlapping with the gingival part of the digital 3D representation of the patient's set of teeth.

In some embodiments, the virtually designed abutment is shaped according to the shape of the gingiva in the implant region. The shape of the abutment may be such that it provides a gentle pressure to the gingiva, such that the contact between the abutment and the gingiva has no gaps. This has the advantage that a good fit between the abutment and the gingiva is provided over the gingiva-abutment interface, such that having the abutment arranged in the mouth results in as little discomfort to the patient as possible.

In some embodiments, a loofting process is applied in the modifying the virtual abutment, such that the surface formed by the loofting provides the contact between the virtual abutment and the virtual crown. The loofting may connect the finish line of the virtual abutment and the virtual margin line of the virtual crown.

In some embodiments, the virtual designing of the crown and abutment is configured to ensure that space for one or more additional layers of the dental restoration, such as a coping layer, is provided.

In some embodiments, the dental restoration comprises a bridge restoration comprising two crowns and two abutments for engaging two implants arranged in the patient's jaw bone.

Disclosed is a system for designing a virtual dental restoration for manufacturing a dental restoration for a patient, said dental restoration comprising an anatomy portion and a sub-gingival portion, wherein the system comprises a non-transitory computer readable medium having one or more computer instructions stored thereon, where said computer instructions comprises instructions for obtaining a virtual anatomy surface expressing a target shape of the anatomy portion of the dental restoration; and creating a virtual sub-gingival surface for the sub-gingival portion of the dental restoration;

where the created virtual sub-gingival surface is shaped such that it contacts the virtual anatomy surface.

Disclosed is computer program product comprising program code means for causing a data processing system to perform the method of any one of the embodiments, when said program code means are executed on the data processing system.

In some embodiments, the computer program product comprises a computer-readable medium having stored there on the program code means.

In some embodiments, at least one step of the method is computer-implemented.

Disclosed is a virtual environment for designing a dental restoration, said virtual environment comprising a virtual work space adapted for providing a virtual abutment and a virtual crown, wherein the virtual environment further comprises a virtual modification tool for modifying the virtual abutment to contact the virtual crown when activated.

In some embodiments, the virtual modification tool is provided as a virtual button.

The present invention relates to different aspects including the method described above and in the following, and corresponding methods yielding one or more of the benefits and advantages described in connection with the first mentioned aspect, and each having one or more embodiments corresponding to the embodiments described in connection with the first mentioned aspect and/or disclosed in the appended claims.

Disclosed is a method of manufacturing at least one part of a dental restoration comprising an anatomy portion and a sub-gingival portion, said method comprising:
  designing a virtual dental restoration using the method according to any of the embodiments;
  manufacturing the at least one part of the dental restoration using direct digital manufacture based on the corresponding part of the designed virtual dental restoration.

Disclosed is a method of manufacturing at least one part of a dental restoration comprising a crown and an abutment, said method comprising:
  designing a virtual dental restoration using the method according to any of the embodiments;
  manufacturing the at least one part of the dental restoration using direct digital manufacture based on the corresponding part of the designed virtual dental restoration.

Disclosed is a system for designing a virtual dental restoration comprising a virtual abutment and a virtual crown, wherein the system comprises a non-transitory computer readable medium having one or more computer instructions stored thereon, where said computer instructions comprises instructions for
  virtually providing a crown,
  virtually providing an abutment, and
  reshaping the abutment to contact the crown.

Disclosed is a method for virtually designing a dental restoration comprising an abutment and a crown, wherein the method comprises,
  virtually providing a crown,
  virtually providing an abutment, and
  reshaping the abutment to contact the crown.

The virtual abutment may define an initial shape of the abutment which then subsequently is reshaped to provide that the abutment contacts the crown while the shape of the virtual crown is maintained while the virtual abutment is modified.

It is an advantage of the method according to the present invention that it is the virtual abutment which is modified rather than the virtual crown since this allows the shape and aesthetics of the virtual crown to be maintained while the modified virtual abutment is shaped to contact the virtual crown.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

Furthermore, the invention relates to a non-transitory computer readable medium storing thereon a computer program, where said computer program is configured for causing computer-assisted virtually designing a dental restoration comprising an abutment and a crown, wherein the method comprises, virtually providing a crown, virtually providing an abutment, and reshaping the abutment to contact the crown.

In some embodiments, the digital 3D representation of the patient's set of teeth have been obtained by an intra-oral scan of at least part of the patient's set of teeth, a scan of at least part of an impression of the patient's set of teeth, and/or a scan of at least part of a model of the patient's set of teeth.

In some embodiments, the 3D scan is performed by means of laser light scanning, white light scanning, probe-scanning, X-ray scanning, and/or CT scanning.

In some embodiments, the method comprises determining the implant position and/or orientation, and where the implant position and/or orientation are taken into account when virtually providing the crown and/or the abutment.

In some embodiments, the method comprises determining an insertion direction of the abutment and/or the crown relative to the patients set of teeth, and where the insertion direction is used in virtually providing the crown and/or the abutment.

Disclosed is a method for virtually designing a dental restoration comprising an abutment and a crown, wherein the method comprises:
  loading a virtual crown to an electronic data processing device, where the virtual crown comprises a virtual crown outer surface bounded by a virtual crown margin line;
  loading a virtual abutment to the electronic data processing device, where the virtual abutment comprises a virtual abutment outer surface having an initial shape; and
  executing one or more computer implemented algorithms using said electronic data processing device, where the algorithms are configured for modifying the virtual abutment such that the shape of the virtual abutment outer surface changes from the initial shape to a final shape in which the virtual abutment outer surface contacts the virtual crown outer surface at least at the virtual crown margin line.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

FIG. 1 shows flowcharts of embodiments of the method for designing a virtual dental restoration.

Figure 1A:
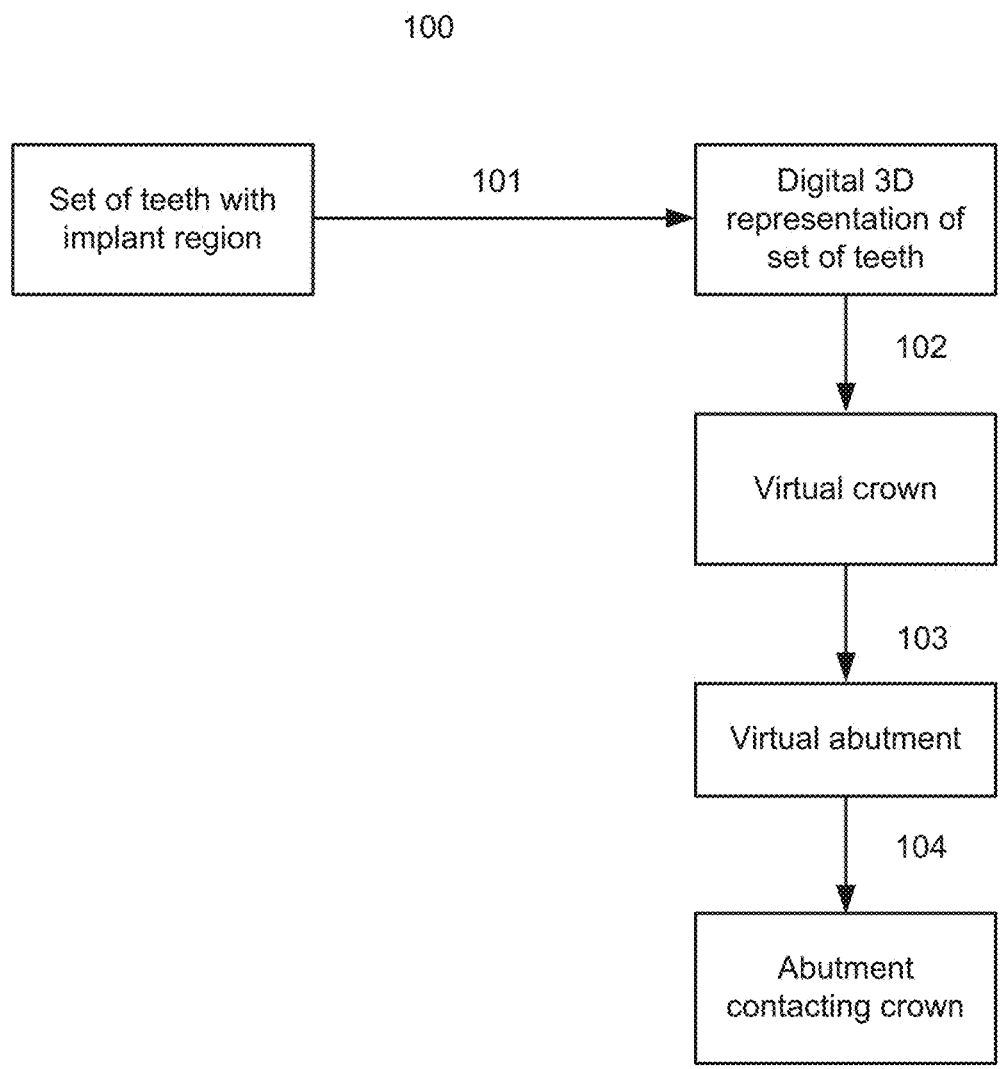
FIGS. 1A and 1B show flowcharts of embodiments of the method for designing a virtual dental restoration.

FIG. 1A shows an example of a flowchart of an embodiment of the method for virtually designing and manufacturing a dental restoration.

In step 101 a digital 3D representation of the patient's set of teeth is obtained, e.g. by direct intra-oral scanning of the set of teeth or by scanning a physical model or an impression of the set of teeth.

In step 102 a virtual crown is obtained. The virtual crown can e.g. be a crown template selected from a crown library or the virtual crown outer surface can be generated using dental CAD software based on the digital 3D representation of the patient's set of teeth In step 103 a virtual abutment is obtained e.g. from an abutment library. The shape of the obtained virtual abutment may be adapted to provide that the surface of the virtual abutment is aligned with the gingiva surrounding the implant into which the abutment is to be secured.

In step 104 the virtual abutment is modified to provide that it contacts the virtual crown such that a functional and aesthetic correct dental restoration can be manufactured from the generated virtual dental restoration. The modifying preferably takes into account the shape of the virtual crown at its margin line such that a smooth transition from the virtual abutment to the virtual crown is obtained.

The dental restoration can subsequently be manufactured based on the designed virtual dental restoration, where the crown and abutment are manufactured as separate units using e.g. a milling machine to form the units from a blank.

Figure 1B:
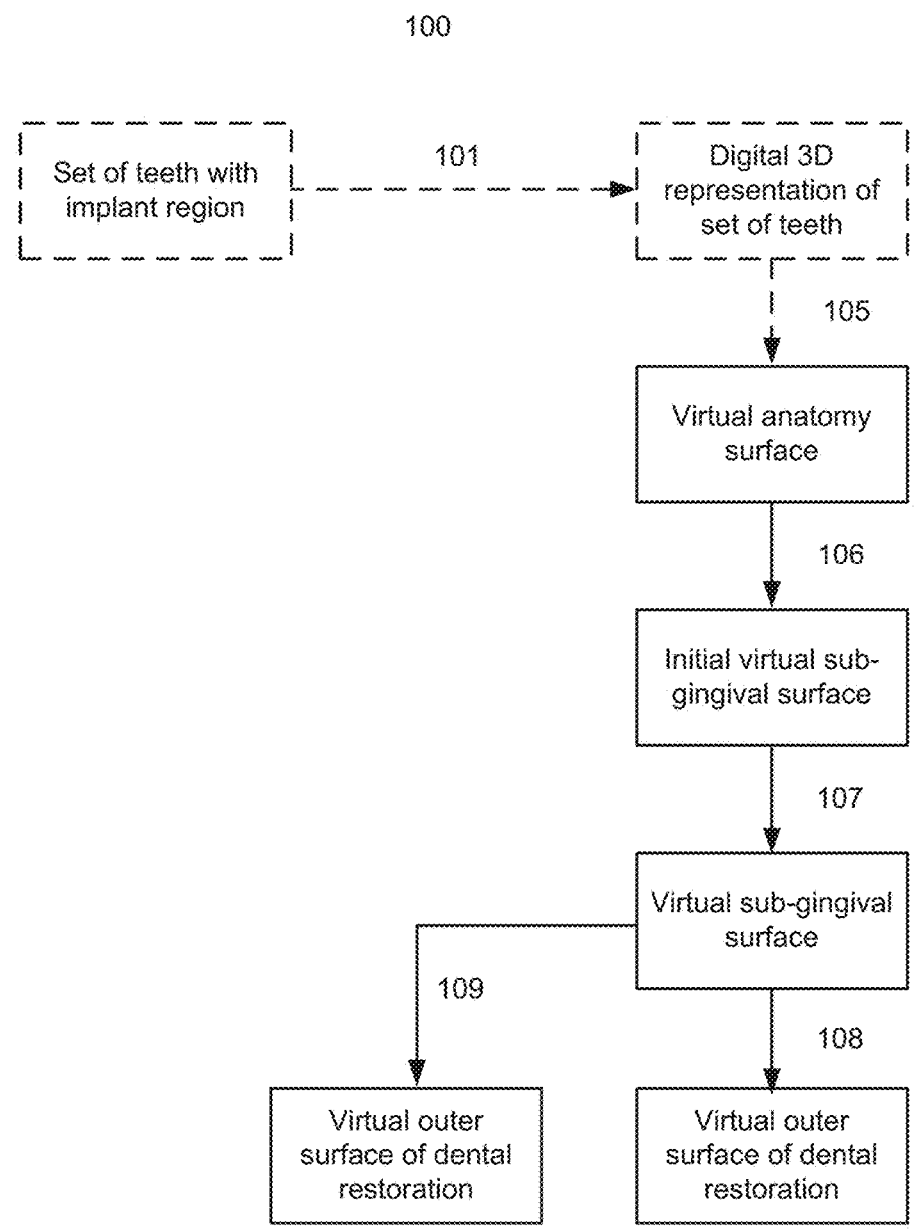

FIG. 1B shows an example of a flowchart for an embodiment of the method for designing a virtual dental restoration for manufacturing a dental restoration for a patient, said dental restoration comprising an anatomy portion and a sub-gingival portion, where the dental restoration is configured for being secured in an implant arranged in the patient's jaw bone.

In step 101, a digital 3D representation of the patient's set of teeth is obtained where the digital 3D representation comprises data relating to the surface of the gingiva in the vicinity of the implant. The digital 3D representation can be obtained by direct intra-oral scanning of the set of teeth or by scanning a physical model or an impression of the set of teeth.

In step 105 a virtual anatomy surface expressing a target shape of the anatomy portion of the dental restoration is obtained.

The virtual anatomy surface can be obtained by e.g. selecting a template anatomy surface from an anatomy surface library and optionally adapting this to fit the digital 3D representation of the patient's set of teeth using dental CAD software. The virtual anatomy surface can also be generating based on data of the digital 3D representation relating to the geometry of the patient's existing teeth, e.g. by mirroring the geometry of the symmetric tooth if this is available in the patient's set of teeth.

In some cases steps 101 and 105 can be omitted, such as when the dental restoration can be designed without taking the shape and relative arrangement of the patient's existing teeth into account.

In step 106 an initial virtual sub-gingival surface is defined from said data of the digital 3D representation relating to the surface of the gingiva in the vicinity of the implant, where the initial virtual sub-gingival surface comprises an initial coronal boundary, i.e. a boundary distal to the implant. The initial virtual sub-gingival surface is preferably configured to follow the part of said digital 3D representation relating to the surface of the gingiva in the vicinity of the implant.

In step 107 the virtual sub-gingival surface is created by:
defining an implant facing boundary for the virtual sub-gingival surface;
projecting the initial coronal boundary of the initial virtual sub-gingival surface onto the virtual anatomy surface to define a coronal boundary of the virtual sub-gingival surface; and
forming the virtual sub-gingival surface such that it extends between the coronal boundary and the implant facing boundary.

Since the formed virtual sub-gingival surface extends to the coronal boundary which is defined at the virtual anatomy surface, the virtual sub-gingival surface will contact the virtual anatomy surface.

The virtual sub-gingival surface describes the shape of the sub-gingival part of the dental restoration which will contact the gingiva in the implant region when the dental restoration is secured in the implant.

Creating the virtual sub-gingival surface from said digital 3D representation allows the operator to design the outer surface of the sub-gingival portion of the dental restoration taking into account the shape of the gingiva in the implant region. The operator can e.g. decide that the manufactured dental restoration shall apply a gentle pressure to the gingiva when secured in the patient's mouth. This can be achieved by creating the virtual sub-gingival surface such that it slightly overlaps with the gingival part of the digital 3D representation of the patient's set of teeth.

The virtual margin line of the virtual dental restoration is defined by the coronal boundary since this is shaped according to the contact between the virtual anatomy surface and the virtual sub-gingival surface.

In step 108 the virtual sub-gingival surface and the part of the virtual anatomy surface coronal to the virtual margin line are combined to form a virtual outer surface of the virtual dental restoration.

Alternatively to the forming of a virtual outer surface of the virtual dental restoration as carried out in step 108, a virtual abutment may be defined at least partly from the virtual sub-gingival surface while a virtual crown may be defined at least partly by the portion of the virtual anatomy surface coronal to the virtual margin line in a step 109.

The dental restoration can subsequently be manufactured using e.g. a milling machine to form the units from a blank based on the designed virtual dental restoration. When the dental restoration comprises an abutment and a crown, the crown and abutment are preferably manufactured as separate units.

Figure 2A:
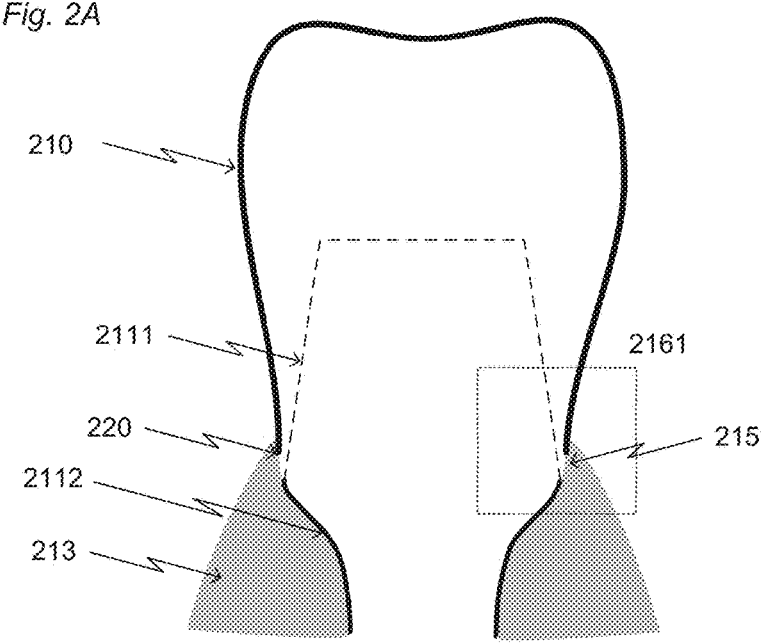
FIGS. 2A, 2B, 2C, 3A, 3B, and 3C show a comparison between the result that can be obtained using the method according to the present invention and the result which can be obtained using a prior art method.
Figures 2B, 2C:
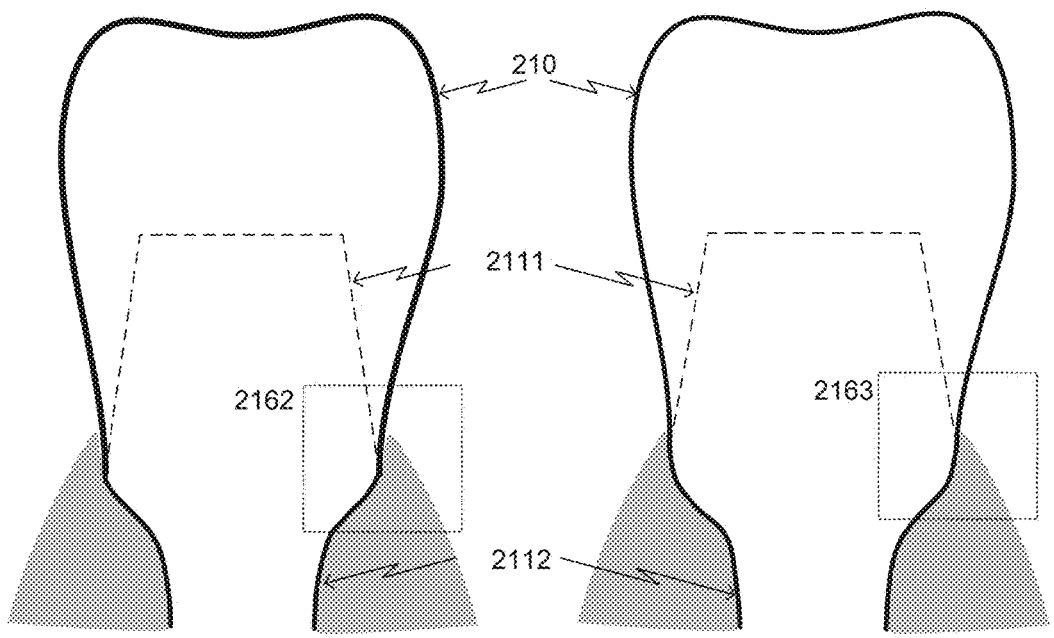
Figure 3A:
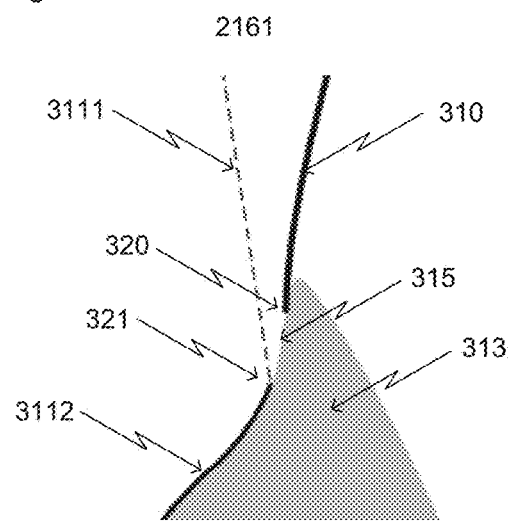
Figure 3B:
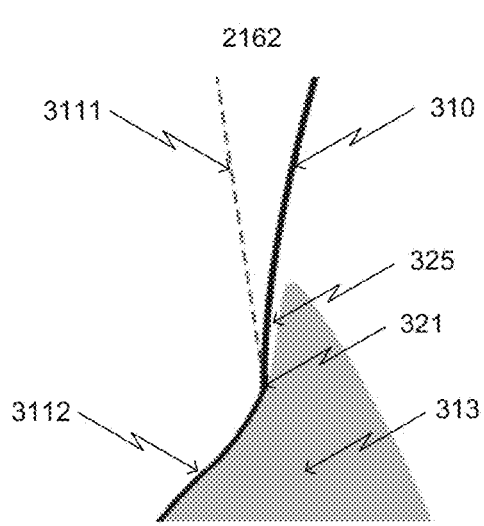
Figure 3C:
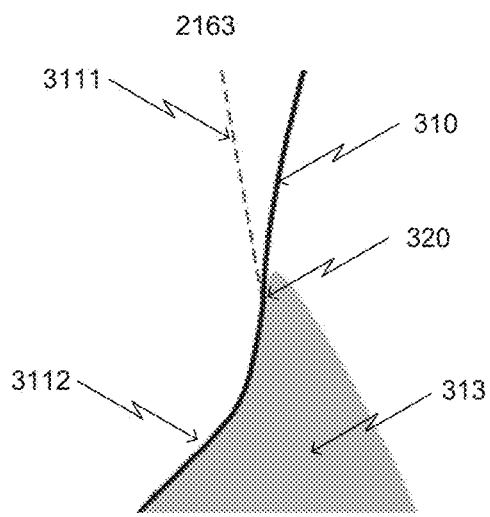

FIGS. 2 and 3 shows a comparison between the result that can be obtained using the method according to the present invention and the result which can be obtained using a prior art method.

The Figures illustrate an example where the dental restoration comprises a crown portion and an abutment for securing the crown at an implant. For simplicity the illustrated example is described using the phrases "virtual crown" and "virtual abutment" instead of the more general phrases "virtual anatomy surface" and "virtual sub-gingival surface".

FIG. 2A shows a virtual crown and a virtual abutment before the virtual abutment is modified to contact the virtual crown.

The obtained virtual crown 210 expresses a target shape of the dental restoration and is shaped such that its margin line 220 extends a few millimeters into the gingiva 213. The virtual abutment has a sub-gingival part 2112 which is shaped according to the gingiva in the implant region and a supra-gingival part 2111 (marked with a dotted line in the figures) which faces the crown inner surface in the manufactured dental restoration. In the case illustrated in the Figures, there is a gap 215 between the margin line of the virtual crown and the finish line of the virtual abutment, which needs to be closed. If the gap is not closed, there a ridge may occur in the surface of the dental restoration which among other things may result in discomfort for the patient.

FIG. 2B shows the prior art method of closing the gap between the virtual crown and the virtual abutment, in which the virtual crown 210 has been modified to contact the sub-gingival part 2112 of the abutment such that the gap is closed.

FIG. 2C shows the result of closing the gap between the virtual crown and virtual abutment using an embodiment of the method according to the present invention. Instead of modifying the virtual crown 210, the sub-gingival part 2112 of the abutment is modified to such that the virtual abutment surface contacts the virtual crown 210 while the shape of the latter is substantially maintained.

In each of FIGS. 2A-2C is marked a region 2161, 2162, and 2163 which includes the gap (in 2161) or the connection made between the virtual abutment and the virtual crown (in 2162 and in 2163). These regions are further discussed in FIG. 3.

FIG. 3 shows close-ups of the regions marked in FIG. 2.

FIG. 3A shows the close-up 2161 of FIG. 2A, with the gap 315 between the virtual abutment 3111, 3112 and the virtual crown 310. The obtained virtual crown is such that its margin line 320 is aligned with a section of the surface of the gingiva 313. Before any modification is performed, the gap 315 extends from the crown margin line 320 to the finish line 321 of the virtual abutment. The finish line 321 divides the sub-gingival part 3112 and the crown facing part 3111 of the abutment surface.

FIG. 3B shows the close-up 2162 of FIG. 2B, with the gap between the sub-gingival surface 3112 of the virtual abutment and the virtual crown 310 being closed by reshaping the virtual crown such that its margin line is brought into contact with the finish line 321 of the virtual abutment, while the shape of the virtual abutment is maintained.

Two disadvantages of this approach are seen in the Figure. Firstly, the crown is now shaped such that a restoration-to-gingiva space 325 is formed between the crown 310 and the gingiva 313. This space is very unfortunate since it may collect food and bacteria such that infections may occur. Further, a kink is defined at the connection between the crown and the abutment, i.e. at the finish line 321, which both may cause discomfort to the patient and destroy the visual aesthetics of the virtual crown which presumably was provided in a perfected shape.

The present invention solves these two problems by modifying the virtual abutment instead of the virtual crown as illustrated in FIG. 3B. FIG. 3B shows the close-up 2163 of FIG. 2C, with the gap between the virtual sub-gingival surface 3112 of the virtual abutment and the virtual crown 310 being closed by modifying the virtual abutment such that virtual sub-gingival surface 3112 contacts the virtual crown at the margin line 320, while the shape of the virtual crown 310 is maintained.

This approach has at least two advantages over the prior art method. Firstly, the restoration-to-gingiva space 325 which was formed when modifying the virtual crown is avoided and a good contact is maintained between the gingiva 313 and the manufactured dental restoration. Secondly, the transition between the abutment and the crown in the manufactured dental restoration is smooth without any kinks or other features.

FIG. 4 shows screen shots of different steps in a workflow for forming a virtual outer surface of the virtual dental restoration. In the illustrated example, the anatomy portion and the sub-gingival portion are integrated parts of a screw-retained crown.

Figure 4A:
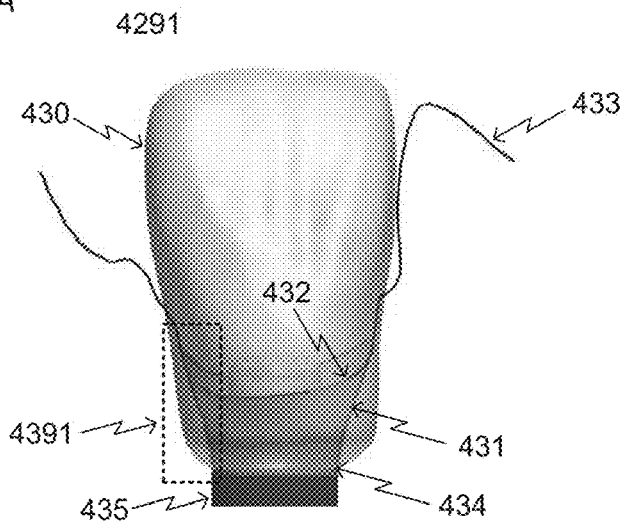
FIGS. 4A-4F show screen shots of different steps in a workflow for forming a virtual outer surface of the virtual dental restoration.

FIG. 4A shows a simulated image 4291 containing an obtained virtual anatomy surface 430 expressing a target shape of the anatomy portion of the dental restoration, an initial virtual sub-gingival surface 431 comprising an initial coronal boundary 432, and a cross sectional representation 433 of a digital 3D representation of the patient's set of teeth. The initial virtual sub-gingival surface 431 is configured to follow the part of said digital 3D representation relating to the surface of the gingiva in the vicinity of the implant. Opposite to the initial coronal boundary 432 the initial virtual sub-gingival surface 431 is bounded by an initial implant facing boundary 434. The initial virtual sub-gingival surface expresses an initial virtual emergence profile for the dental restoration.

Figure 4B:
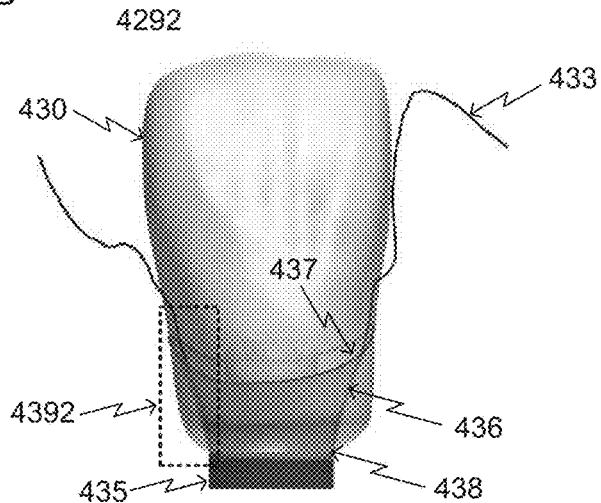

FIG. 4B shows a simulated image 4292 containing the obtained virtual anatomy surface 430 and the cross sectional representation 433 of the digital 3D representation of the patient's set of teeth also illustrated in FIG. 4A. In FIG. 4B the simulated image 4292 contains a virtual sub-gingival surface 436 for the sub-gingival portion of the dental restoration instead of the initial virtual sub-gingival surface seen in FIG. 4A. The created virtual sub-gingival surface 436 is bounded by a coronal boundary 437 defined by projecting the initial coronal boundary onto the virtual anatomy surface 430 such that the virtual sub-gingival surface contacts the virtual anatomy surface. The virtual sub-gingival surface 436 is further bounded by an implant facing boundary 438. The contact between the virtual anatomy surface and the virtual sub-gingival surface defines a virtual margin line of the virtual dental restoration.

FIGS. 4A and 4B further show frames 4391, 4392 enclosing similar part of the simulated images of FIGS. 4A and 4B. These parts are seen enlarged in FIGS. 4D and 4E. Also seen in FIGS. 4A and 4B (as well as in FIGS. 4C-4E) is the crown facing part of the retention screw 435 of the screw-retained crown. The full retention screw can be seen in FIG. 4E.

Figure 4C:
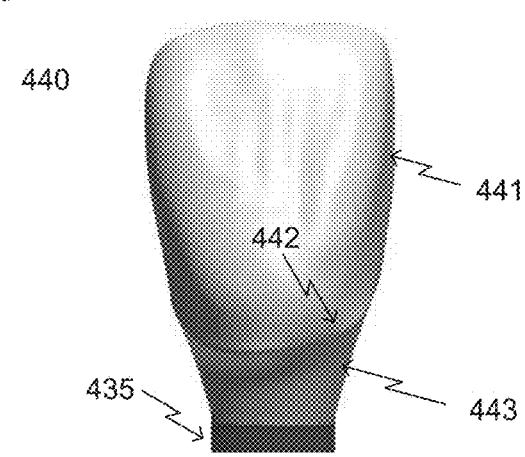

FIG. 4C shows a virtual outer surface 440 of the virtual dental restoration formed by combining the virtual sub-gingival surface 436 and the part of the virtual anatomy surface 430 defined by the contact between the virtual anatomy surface and the virtual sub-gingival surface, i.e. by the shape of the coronal boundary 437 which defines the virtual margin line 442 for the dental restoration.

The portion 441 of the virtual outer surface arranged coronal to the margin line 442 is shaped according to the corresponding portion of the obtained virtual anatomy surface, while the sub-gingival portion, i.e. the portion 443 arranged between the retention screw 435 and the margin line 442 is shaped according to the created virtual sub-gingival surface. The shape of the anatomy surface above the margin line is hence not changed when the virtual anatomy surface and the virtual sub-gingival surface are combined to form the virtual outer surface 440 of the virtual dental restoration.

Figure 4D:
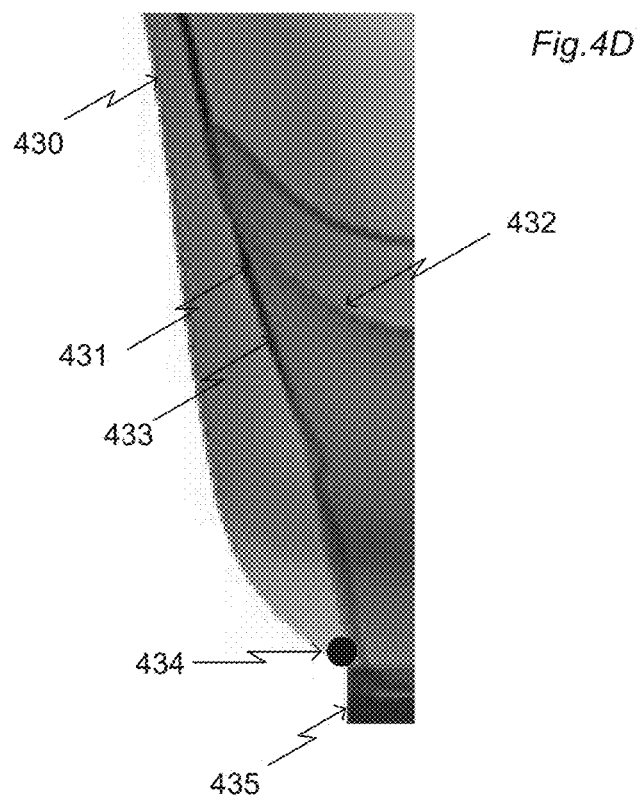

FIG. 4D shows a close-up of the section of the simulated image 4291 marked by the frame 4391 in FIG. 4A. In the close-up it is seen more clearly that the initial virtual sub-gingival surface 431 follows the part of said digital 3D representation 433 relating to the surface of the gingiva in the vicinity of the implant. The initial virtual sub-gingival surface 431 extends along the digital 3D representation 433 between the initial coronal boundary 432 and the initial implant facing boundary 434 located at the retention screw 435. It is also seen that the initial virtual sub-gingival surface does not contact the obtained virtual anatomy surface 430.

Figure 4E:
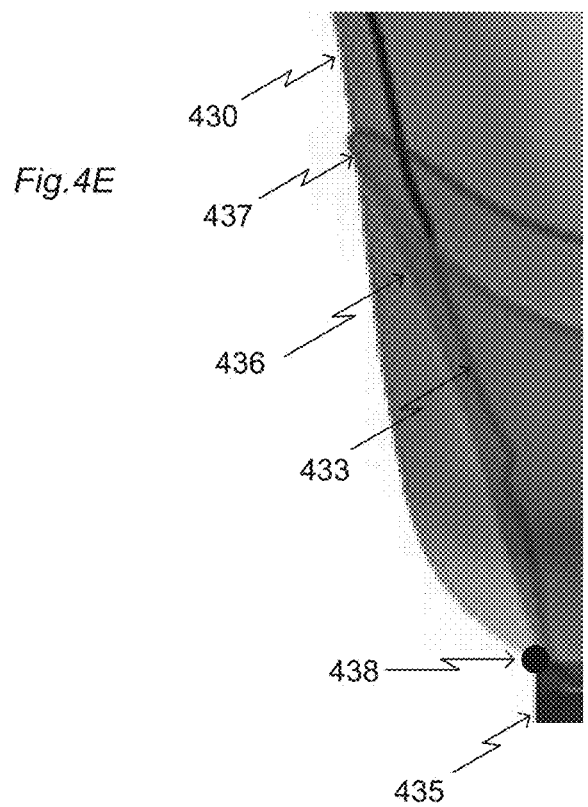

FIG. 4E shows a close-up of the section of the simulated image 4292 marked by the frame 4392 in FIG. 4B.

FIG. 4E shows the coronal boundary 437 defined by projecting the initial coronal boundary onto the virtual anatomy surface 430. The virtual sub-gingival surface 436 for the sub-gingival portion of the dental restoration is created by forming a virtual surface which is bounded by the coronal boundary 437 and an implant facing boundary 438 located at the retention screw 435.

This approach provides that the virtual sub-gingival surface 436 contacts the virtual anatomy surface 430 and that the outer surface of the dental restoration manufactured from the virtual dental restoration is not distorted which may be the case in the prior art methods where the anatomy portion connects to the virtual sub-gingival surface.

The implant facing boundary 438 can be defined by copying the initial implant facing boundary.

Given that the virtual sub-gingival surface 436 extends slightly beyond the gingival part of the digital 3D representation 433 of the patient's set of teeth, the manufactured dental restoration will provide a gentle pressure on the gingiva when secured in the implant 435 which is advantageous in many cases.

The virtual sub-gingival surface 436 can be created using computer implemented algorithms executed on a data processing device, where the algorithms may be configured for maintaining the smoothness of the initial virtual sub-gingival surface.

Figure 4F:
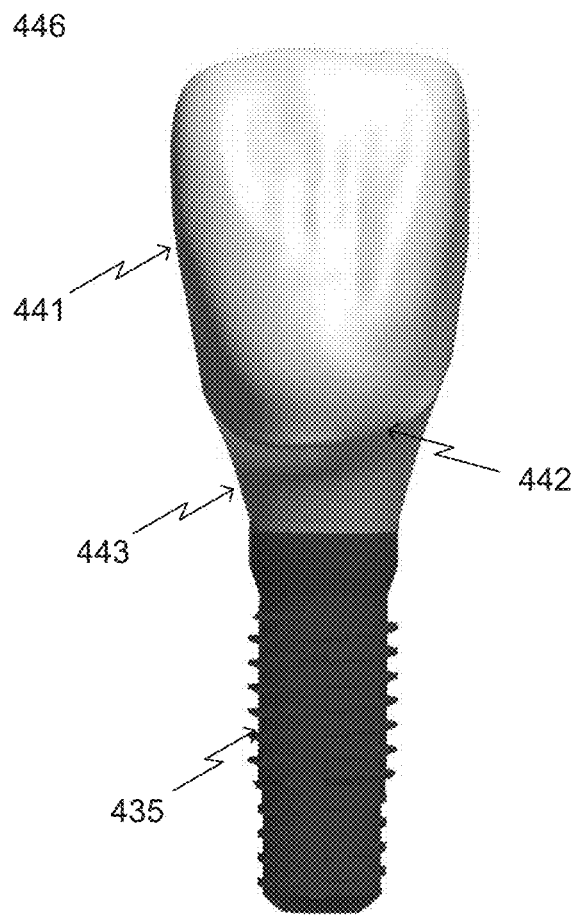

FIG. 4F shows the generated virtual dental restoration 446 with a retention screw 435 configured for engaging an implant arranged in the patient's jaw bone. The retention screw can be part of the dental restoration or be an independent unit which engages the implant through a bore defined through the dental restoration. The portion 441 of the virtual outer surface arranged coronal to the margin line 442 is shaped according to the corresponding portion of the obtained virtual anatomy surface, while the sub-gingival portion 443 is shaped according to the created virtual sub-gingival surface.

The dental restoration can then be manufactured from the virtual dental restoration using standard CAM technology. If the screw 435 is an integrated part of the dental restoration, it can be permanently attached by e.g. gluing it to the sub-gingival portion.

FIG. 5 illustrates an advantage of the invention over the prior art.

Figure 5A:
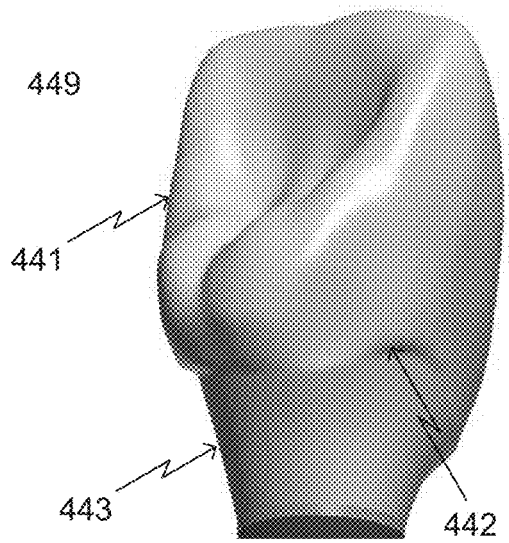
FIGS. 5A and 5B illustrate an advantage of the invention over the prior art.
Figure 5B:
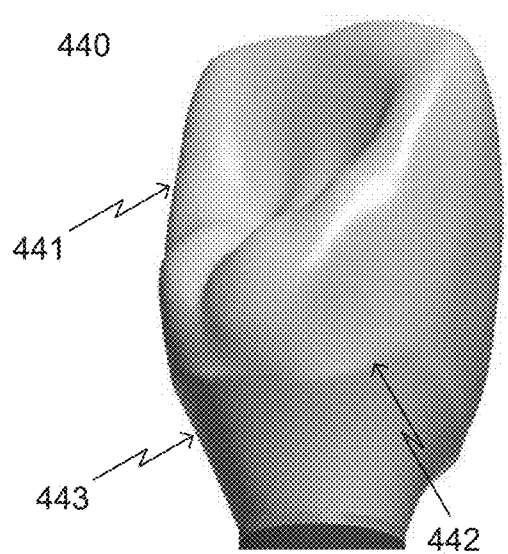

FIGS. 5A and 5B illustrate virtual outer surfaces of virtual dental restorations that are designed based on the same obtained virtual anatomy surface and the same initial virtual sub-gingival surface.

FIG. 5A, shows the result of the prior art method in which the virtual outer surface 449 is designed by deforming the obtained virtual anatomy surface such that it contacts the initial virtual sub-gingival surface.

FIG. 5B shows the result of an embodiment of the method according to the invention, where a virtual sub-gingival surface is formed by modifying an initial virtual sub-gingival surface such that the formed virtual sub-gingival surface contacts the virtual anatomy surface. It is hence the sub-gingival part of the virtual outer surface of the dental restoration, i.e. the part not seen when the dental restoration is seated in the patient's mouth, which is deformed and not the visible anatomy surface.

Further in cases where the circumference of the anatomy surface is larger than that of the initial virtual sub-gingival surface at the coronal boundary of the latter, the dental restoration will have kinks at the margin line 442, i.e. at the transition between the sub-gingival portion 443 and the anatomy portion 442 as illustrated in FIG. 5A.

In FIG. 5B the transition between the sub-gingival portion 443 and the anatomy portion 442 is much smoother and no kinks are seen.

Figure 6:
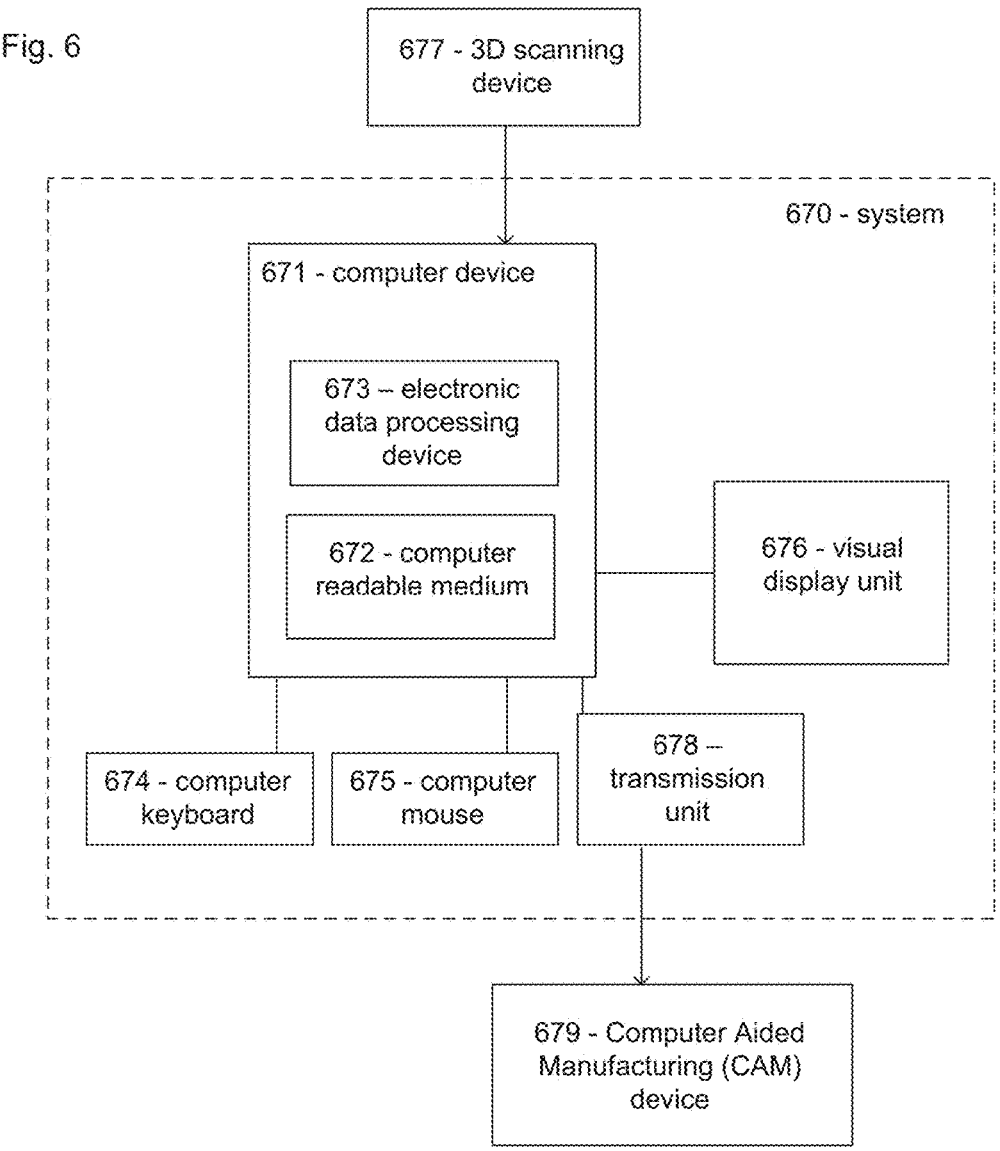
FIG. 6 shows a schematic of a system according to an embodiment of the invention

FIG. 6 shows a schematic of a system according to an embodiment of the invention. The system 670 comprises a computer device 671 comprising a computer readable medium 672 and an electronic data processing device 673, such as a microprocessor. The system further comprises a visual display unit 676, a computer keyboard 674 and a computer mouse 675 for entering data and activating virtual buttons visualized on the visual display unit 676. The visual display unit 676 can be a computer screen. The computer device 671 is capable of obtaining a virtual anatomy surface expressing a target shape of the anatomy portion of the dental restoration, e.g. by loading the virtual anatomy surface into the electronic data processing device 673, and of executing one or more computer implemented algorithms using said electronic data processing device: The algorithms are configured for creating a virtual sub-gingival surface for the sub-gingival portion of the dental restoration where the created virtual sub-gingival surface is shaped such that it contacts the virtual anatomy surface. The computer device is further capable of forming a virtual restoration surface by executing further algorithms configured for combining the virtual sub-gingival surface with part of the virtual anatomy surface.

The computer device 671 is further capable of receiving a digital 3D representation of the patient's set of teeth from a 3D scanning device 677, such as the TRIOS intra-oral scanner manufactured by 3shape TRIOS A/S, or capable of receiving scan data from such a 3D scanning device and forming a digital 3D representation of the patient's set of teeth based on such scan data. The received or formed digital 3D representation can be stored in the computer readable medium 672 and provided to the electronic data processing device 673. Based on the digital 3D representation an initial virtual sub-gingival surface bounded by an initial coronal boundary can be defined.

When creating the virtual sub-gingival surface of the dental restoration and optionally also when combining this surface with the obtained virtual anatomy surface, one or more options can be presented to the operator, such as whether to project an initial coronal boundary of an initial virtual sub-gingival surface onto the virtual anatomy surface. These options can be presented in a virtual environment visualized on the visual display unit 676.

The system comprises a unit 678 for transmitting the virtual dental restoration, such as the virtual crown and virtual abutment of an abutment-crown dental restoration, to e.g. a computer aided manufacturing (CAM) device 679 for manufacturing the dental restoration or to another computer system e.g. located at a milling center where the dental restoration is manufactured. The unit for transmitting can be a wired or a wireless connection.

The 3D scanning of the patient's set of teeth using the 3D scanning device 677 can be performed at a dentist while creating the virtual sub-gingival surface and combining this with the virtual anatomy surface to generate the virtual dental restoration can be performed at a dental laboratory. In such cases the digital 3D representation of the patient's set of teeth can be provided via an internet connection between the dentist and the dental laboratory.

Figure 7:
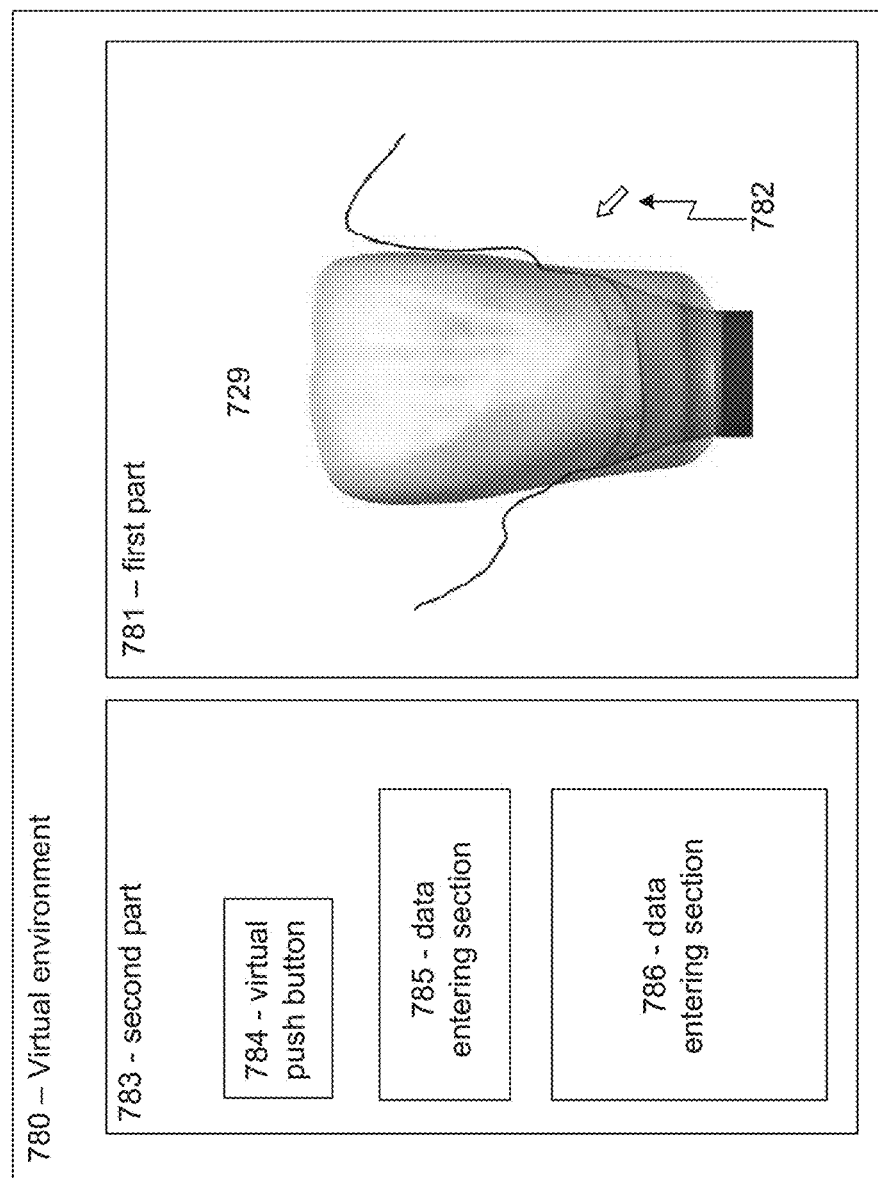
FIG. 7 shows a schematic of a virtual environment according to an embodiment of the invention.

FIG. 7 shows a schematic of a virtual environment according to an embodiment of the invention.

In FIG. 7 a first part 781 of the virtual environment 780 is seen in which a simulated image 729 created by superimposing the virtual anatomy surface, an initial virtual sub-gingival surface and a digital 3D representation of the patient's set of teeth. In the figure, a cross section of the digital 3D representation of the patient's set of teeth is depicted. A virtual tool 782 can used in marking or defining different features such as the initial coronal boundary of an initial virtual sub-gingival surface e.g. by controlling the arrangement of control points used to shape e.g. a 3D spline used to describe the initial coronal boundary. The virtual movement tool can be configured for grabbing the simulated image and moving it in the virtual environment using e.g. a computer mouse.

The second part 783 of the virtual environment comprises data entering sections 785, 786 for entering various data relevant for the procedure, such as data relating to which type of anatomy surface is to be obtained and the direction of a projection of the initial coronal boundary onto the virtual anatomy surface.

A virtual push button 784 is configured for creating the virtual sub-gingival surface taking into account the data entered in the data entering sections 785, 786. The virtual environment can be visualized on a visual display unit, such as a computer screen being part of a system configured for implementing the method according to the present invention.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for designing a virtual abutment for manufacturing an abutment part of a dental restoration for a patient, said dental restoration further comprising a crown configured for being seated at the abutment, wherein the method comprises:
    loading a virtual anatomy surface into an electronic data processing device, said virtual anatomy surface expressing a target shape of the crown portion of the dental restoration;
    loading an obtained virtual abutment comprising a virtual abutment finish line into the electronic data processing device, wherein the abutment finish line divides an abutment surface into a gingival facing part and a crown facing part;
    modifying the obtained virtual abutment by executing one or more computer implemented algorithms using said electronic data processing device, where the algorithms are configured to adapt a shape of the obtained virtual abutment such that the virtual abutment finish line of the modified virtual abutment is in contact with the virtual anatomy surface.

2. The method according to claim 1, where the contact between the virtual anatomy surface and the modified virtual abutment defines a virtual margin line of the virtual dental restoration.

3. The method according to claim 2, wherein the algorithms are configured to provide that the modified virtual abutment has a smooth transition to the virtual anatomy surface at the virtual margin line.

4. The method according to claim 1, wherein the method comprises obtaining a digital 3D representation of the patient's set of teeth, said digital 3D representation comprising data relating to the surface of the patient's gingiva.

5. The method according to claim 4, where the obtained virtual abutment is configured to follow the part of said digital 3D representation relating to the surface of the gingiva in the vicinity of an implant.

6. A method for designing a virtual abutment for manufacturing an abutment part of a dental restoration for a patient, said dental restoration further comprising a crown configured for being seated at the abutment, wherein the method comprises:
    loading a virtual anatomy surface into an electronic data processing device, said virtual anatomy surface expressing a target shape of the crown portion of the dental restoration;

loading an obtained virtual abutment comprising a virtual abutment finish line into the electronic data processing device;

modifying the obtained virtual abutment by executing one or more computer implemented algorithms using said electronic data processing device, where the algorithms are configured to adapt a shape of the obtained virtual abutment such that the virtual abutment finish line of the modified virtual abutment is aligned with the virtual anatomy surface, wherein modifying the obtained virtual abutment comprises virtually snapping the obtained virtual abutment to the virtual anatomy surface in a manner providing that surfaces of the modified virtual abutment and the virtual anatomy surface are aligned or connected with the modified virtual abutment and the virtual crown together defining an outer surface of the dental restoration.

7. The method according to claim 6, wherein the outer surface is smooth.

8. A method for designing a virtual abutment for manufacturing an abutment part of a dental restoration for a patient, said dental restoration further comprising a crown configured for being seated at the abutment, wherein the method comprises:

loading a virtual anatomy surface into an electronic data processing device, said virtual anatomy surface expressing a target shape of the crown portion of the dental restoration;

loading an obtained virtual abutment comprising a virtual abutment finish line into the electronic data processing device;

modifying the obtained virtual abutment by executing one or more computer implemented algorithms using said electronic data processing device, where the algorithms are configured to adapt a shape of the obtained virtual abutment such that the virtual abutment finish line of the modified virtual abutment is aligned with the virtual anatomy surface, wherein modifying the obtained virtual abutment comprises projecting the virtual abutment finish line onto the virtual anatomy surface to define the finish line of the modified virtual abutment and forming a virtual surface that extends between the defined finish line of the modified virtual abutment and an implant facing boundary.

9. The method according to claim 8, wherein the projecting is substantially parallel to the occlusal plane of the patient.

10. A method for virtually designing a dental restoration comprising an abutment and a crown, wherein the method comprises:

loading a virtual crown to an electronic data processing device, where the virtual crown comprises a virtual crown outer surface bounded by a virtual crown margin line which is arranged substantially at the gum line;

loading a virtual abutment to the electronic data processing device, where the virtual abutment comprises a virtual abutment outer surface having an initial shape; and executing one or more computer implemented algorithms using said electronic data processing device, where the algorithms are configured to modify the virtual abutment such that a shape of the virtual abutment outer surface changes from the initial shape to a final shape in which the virtual abutment outer surface contacts the virtual crown outer surface at the virtual crown margin line.

11. The method according to claim 10, where the shape of the virtual crown is maintained while the virtual abutment is modified such that the shape and aesthetics of the virtual crown is maintained.

* * * * *